United States Patent [19]

Konishi

[11] Patent Number: 4,858,604
[45] Date of Patent: Aug. 22, 1989

[54] ADHESIVE BANDAGE

[75] Inventor: Ryusaku Konishi, Takarazuka, Japan

[73] Assignee: Nippon Zoki Pharmaceutical Co., Ltd., Osaka, Japan

[21] Appl. No.: 775,836

[22] Filed: Sep. 13, 1985

Related U.S. Application Data

[63] Continuation of Ser. No. 447,640, Dec. 7, 1982, abandoned.

[30] Foreign Application Priority Data

Dec. 9, 1981 [JP] Japan .................... 56-198879
Dec. 14, 1981 [JP] Japan .................... 56-186996

[51] Int. Cl.$^4$ .................................... A61L 15/00
[52] U.S. Cl. .................................... 128/156; 604/306
[58] Field of Search .............. 128/156, 155; 604/306, 604/304, 307

[56] References Cited

U.S. PATENT DOCUMENTS

| | | | |
|---|---|---|---|
| 2,209,914 | 7/1940 | Gerber et al. | 604/306 |
| 2,489,675 | 11/1949 | Roberts | 128/156 |
| 2,579,403 | 12/1951 | Slomowitz et al. | 604/306 |
| 2,595,606 | 5/1952 | Pohjola | 604/306 |
| 2,629,378 | 2/1953 | Barton | 604/307 |
| 2,714,382 | 8/1955 | Alcala | 128/156 |
| 2,817,336 | 12/1957 | Kravitz et al. | 604/306 |
| 3,297,032 | 1/1967 | Antonik | 604/306 |
| 3,814,095 | 6/1974 | Lubens | 128/260 |
| 4,117,841 | 10/1978 | Perrotta et al. | 128/155 |

Primary Examiner—Richard J. Apley
Assistant Examiner—J. Welsh
Attorney, Agent, or Firm—Frank P. Presta

[57] ABSTRACT

An adhesive bandage comprising a pad for absorbing a medicine which is separately stored from the pad by means of a medicine covering film interposed between the medicine and the adhesive tape or by means of a capsule enclosing the medicine in it until the bandage is applied to a local site of body such as wound, an adhesive tape carrying the pad thereon, a release sheet provided with a blister portion adapted to placing the medicine in it and attached to the adhesive tape in such a manner that the open side of the blister may face the adhesive tape.

17 Claims, 5 Drawing Sheets

# ADHESIVE BANDAGE

CROSS REFERENCE TO RELATED APPLICATION

This is a continuation of application Ser. No. 447,640, filed Dec. 7, 1982 now abandoned.

BACKGROUND OF THE INVENTION

1. Field of the invention

This invention relates to an adhesive bandage.

2. Description of the Prior Art

An adhesive bandage which is in common use comprises a gauze pad impregnated with a disinfectant, wound healing agent and an ointment, a porous adhesive tape carrying the gauze pad thereon and a release sheet covering the adhesive tape. The release sheet is removed when the gauze pad is applied to a local site of the body such as wound. The adhesive bandage, however, is liable to lose its effect with the lapse of time, since the medicine with which the gauze pad has been impregnated is gradually lost by vaporization. Thus the gauze pad becomes dry, and is likely to hurt the wound or give rise to a pain when it is applied thereto.

SUMMARY OF THE INVENTION

It is an object of this invention to provide an adhesive bandage having a pad to which a fresh medicine is supplied when it is applied to a local site of the body.

It is another object of this invention to provide an adhesive bandage holding a medicine in such a manner that its effect may not be lost for a long time.

It is still another object of this invention to provide an adhesive bandage which can be applied to a wound without hurting it or giving rise to a pain.

It is a further object of this invention to provide an adhesive bandage in which the medicine maintains its effect, for a prolonged period, for achieving any desired sterilizing, disinfecting and curing purposes.

According to the adhesive bandage of this invention, the medicine is held by a release sheet or by a capsule separately from a pad on an adhesive tape during its storage, and is caused to impregnate the pad with it when it is applied to a wound.

Other objects and features of the present invention will be more apparent to those skilled in the art on consideration of the accompanying drawings and following specification wherein are disclosed several exemplary embodiments of the invention with the understanding that such variations, modifications and elimination of parts may be made therein as fall within the scope of the appended claims without departing from the spirit of the invention.

DETAILED DESCRIPTION OF THE INVENTION

The adhesive bandage of this invention comprises an adhesive tape carrying a pad thereon, and a release sheet holding a medicine separately from the pad. The medicine may be held separately from the pad, in a blister (recessed portion) provided on a release sheet, for example, by an interposing film between the medicine and the pad, or by being encapsulated in a capsule which in turn is placed in the blister. The release sheet is attached to the adhesive tape in such a manner that the open side of the blister portion may face to the pad on the adhesive tape.

Figure 1:
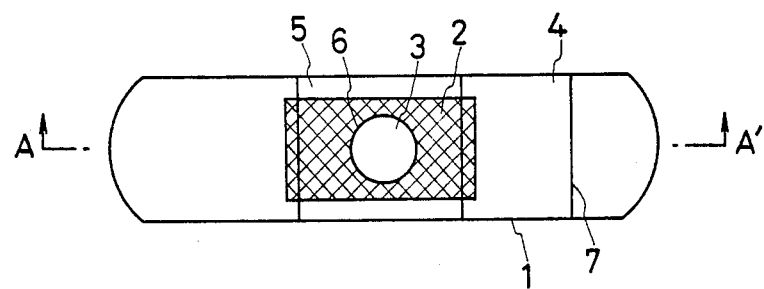
FIG. 1 is a schematic top plan view of an adhesive bandage embodying this invention.
Figure 2:
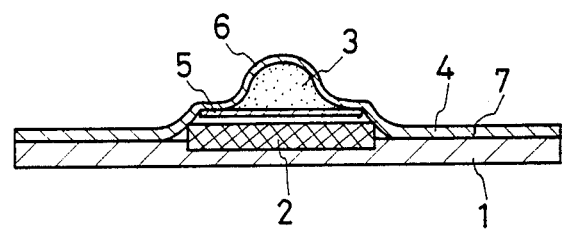
FIG. 2 is a sectional view of the embodiment taken along the line A—A' of FIG. 1.

The invention will be described in more detail by way of example with reference to the drawings. Referring first to FIGS. 1 and 2, an adhesive bandage embodying this invention comprises an adhesive tape 1 carrying a pad 2 thereon, and a medicine 3 enclosed in a space defined between a medicine covering film 5 and a blister 6 formed on a release sheet 4. The release sheet 4 may be provided at one end with a slit 7 along which the release sheet 4 may be bent so that it may be easily removed. The adhesive bandage can, for example, be made as will hereinafter be described. An appropriate quantity of the medicine is put into a blister (recess) formed at a predetermined position of the release sheet 4, and the recess is sealed with the medicine covering film 5 by the PTP (press-through pack) method. Then, the release sheet 4 is attached to the adhesive tape 1 carrying a pad thereon in such a manner that the film 5 may face the pad 2.

The adhesive bandage of this invention may contain various kinds of medicines, for example, a sterilizer or disinfectant, a wound astringent healing promoter, a hemostatic agent, an anti-inflammatory agent, an antihistamine, and a local anesthetic. Specific examples of the sterilizer or disinfectant include chlorhexidine gluconate, benzalkonium chloride, chloroxylenol, acrinol, thianthol, dequalinium chloride, sulfisomidine, sulfamine, nitrofurazone, boric acid, homosulfamine, and triclocarban. Examples of the healing promoter include zinc oxide, pyridoxine hydrochloride, tocopherol acetate, and pyridoxine dipalmitate. Examples of the hemostatic agent include naphazoline hydrochloride, zinc sulfate, and ephedrine hydrochloride. Examples of the anti-inflammatory agent include steroids such as prednisolone, dexamethasone, cortisone acetate and other steroids, glycyrrhetinic acid, and lysozyme chloride. Examples of the antihistamine include chlorophenilamine maleate and diphenhydramine hydrochloride. Examples of the local anesthetic include lidocaine, ethyl aminobenzoate, procaine hydrochloride, dibucaine hydrochloride, tetracaine hydrochloride, and diethyl aminoethyl p-butylamino-benzoate hydrochloride.

These medicines may be used singly or in combination depending upon intended purposes. They may be in the form of a solution, ointment, grease or powder, or any other form as long as they are fluid. If appropriate, a solution may be adsorbed into a carrier such as sponge or cotton and thereafter enclosed in the blister.

The adhesive tape may be of any ordinary material and construction and preferably it is porous. If required, the adhesive tape may have a recessed center to place the pad, and a waterproof rear surface which is obtained by any customary method.

The pad may be formed from absorbent cotton or any other type of cotton, an unwoven fabric, paper, sponge, or any other liquid-absorbent material.

The release sheet may be formed from polyvinyl chloride, or any other synthetic resin, and provided with a circular, oval or rectangular blister in its center. The release sheet may also be provided at one end with a slit which facilitates its removal. The medicine covering film covers the bottom of the blister on the release tape to keep the medicine apart from the pad until the pad is applied to a wound. The film may be formed from, for example, aluminum foil or glassine paper, and bonded to the release sheet to form a press-through pack (PTP). The film may be so sized as to cover the medicine alone, or cover the whole bottom surface of the release sheet. When a large bandage is required, a plurality of blisters may be provided per one pad.

Figure 3:
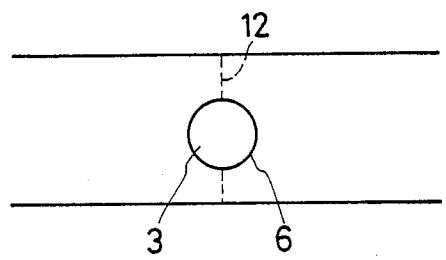
FIG. 3 is a top plan view of a PTP (press-through pack) release sheet according to another embodiment of this invention.
Figure 4:
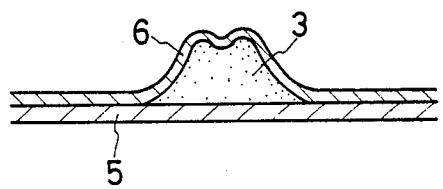
FIGS. 4 and 5 are sectional views showing modified medicine covering films and release sheets of PTP.
Figure 5:
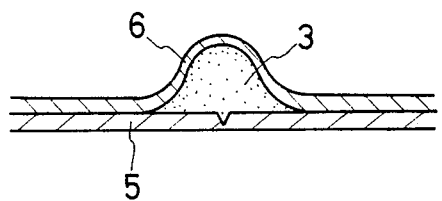
Figure 6:
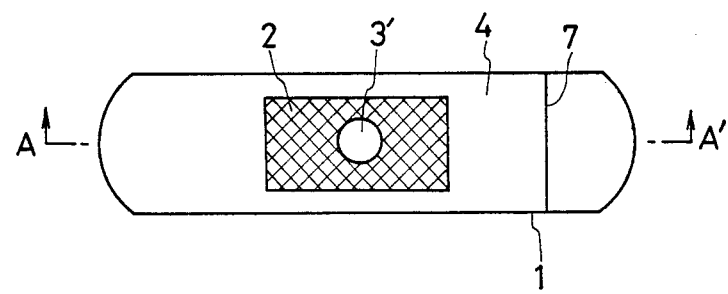
FIG. 6 is a top plan view of an adhesive bandage according to still another embodiment of this invention.
Figure 7:
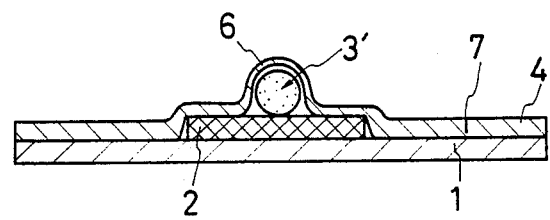
FIG. 7 is a sectional view of the embodiment taken along the line A-A' of FIG. 6.
Figure 8:
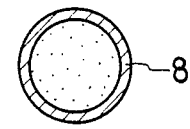
FIG. 8 is a cross sectional view of a capsule in the adhesive bandage of this invention.
Figure 11:
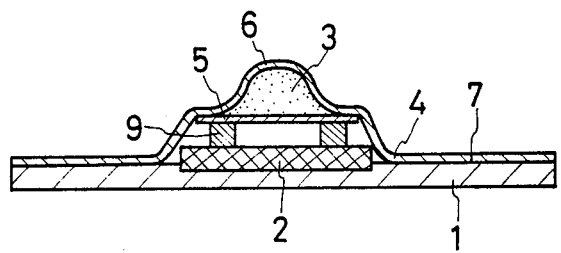
FIGS. 11, 12 and 13 are sectional views of further embodiments of this invention.

When the adhesive bandage is to be applied to a wound, a finger pressure is applied to the blister 6 to rupture the medicine covering film 5 to cause the medicine 3 to flow onto the pad 2. Then, the release sheet 4 is bent along the slit 7, and removed from the adhesive tape 1. Thereafter, the pad 2 is applied to the wound. Thus, the adhesive bandage of the invention has the following advantages. The bandage ensures a fresh supply of medicine on the pad when it is applied to the wound. The medicine does not lose its effect during the storage of the bandage. The pad can be applied to the wound without hurting it. The medicine maintains its efficacy, for a prolonged period to achieve any desired sterilizing, disinfecting and curing purposes. The bandage has an additional advantage that it permits the visual observation of the medicine from the outside if the blister portion is made transparent. The adhesive bandage may be provided with a line of perforations 12 along each side of the blister on the release sheet as shown in FIG. 3. The perforations 12 ensure that the medicine covering film be easily ruptured without remaining on the pad when the blister is bent or pressed. The rupturing of the medicine covering film can also be facilitated if the blister is provided with a V- or U-shaped recess at its top as shown in FIG. 4, or if the film is provided with a slit 13, as shown in FIG. 5. If the blister is provided with a V- or U-shaped recess at its top, the medicine covering film can be ruptured by the bottom of the V- or U-shaped recess. The rupturing of the medicine covering film can further be facilitated if a ring 9 is provided between the film 5 and the pad 2 as shown in FIG. 11. In this case, a space is provided by the ring so that the film 5 may be easily ruptured and the broken film can be prevented from remaining on the pad. The ring is of course removed when the pad is applied. The ring may be made from an appropriate material such as plastics.

Referring now to FIGS. 6 to 10, an adhesive bandage according to another embodiment of this invention includes a capsule enclosing the medicine. The same or like numerals are used to designate the same or like parts or components throughout the accompanying drawings. In the bandage shown in FIGS. 6 to 10, instead of being stored by the medicine covering film the medicine is encapsulated in the capsule 8 which in turn is placed in the blister 6 on the pad, so that the medicine may be stored separately from the pad. A reference numeral 3' denotes encapsulated medicine. Any medicine or medicines may be selected from among those hereinbefore listed by way of example. The capsule is formed from gelatin, or any other pharmaceutically acceptable film forming material that does not react with the medicine. The form of the capsule may be selected depending on the desired purposes and it may be, for example, sphere, cylinder, cone or square column. In order to be placed in a gelatin capsule, the medicine is usually dissolved or suspended in a vegetable oil, such as sesame, peanut or olive oil. The medicine does not necessarily need to be in the form of a solution, but may be in the form of an ointment, grease or powder, or any other form if it is free flowing. The use of a solution is, however, most desirable when the medicine is placed in the capsule.

When the bandage is to be applied to a wound, a finger pressure is applied to the blister 6 to rupture the capsule 8 to cause the medicine to flow from the capsule to the pad. Then, the release sheet 4 is bent along its slit 7, and removed from the adhesive tape 1, whereby the pad 2 holding a fresh supply of medicine is exposed for application to the wound. The same advantages as described above can be achieved by the bandage of this type. The medicine does not lose its effect during the storage of the bandage, since it is enclosed in the capsule immediately before the use of the bandage. The pad can be applied to the wound without hurting it and give rise to a pain, since it is wetted with the medicine immediately prior to its application. The medicine can maintain its efficacy for a prolonged period for achieving any desired sterilizing, disinfecting and curing purposes. And also the bandage permits the visual observation of the medicine if the capsule and the blister portion are transparent.

The bandage may have a plurality of capsules depending on the sizes of the pad and the bandage.

When the capsule 8 is ruptured, its fragments adhere closely to the inner wall surface of the blister, and do not remain on the pad, if the blister is provided with an irregular or uneven inner surface. Even if any fragment of the capsule material may be left on the pad, it does not give rise to any problem if the capsule is formed from pharmaceutically acceptable material such as gelatin. If desired, an adhesive may be applied on the inner surface of the blister so as to remove the ruptured capsule attaching to the release sheet.

Figure 9:
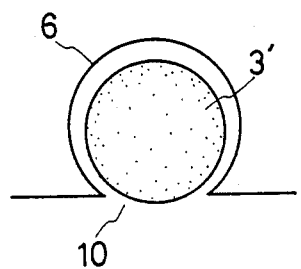
FIGS. 9 and 10 are sectional views of blisters according to further embodiments of this invention.
Figure 10:
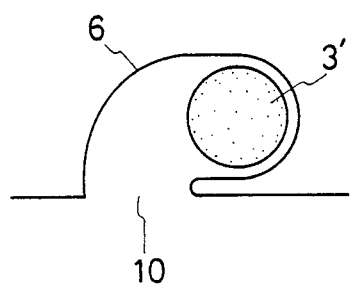
Figure 12:
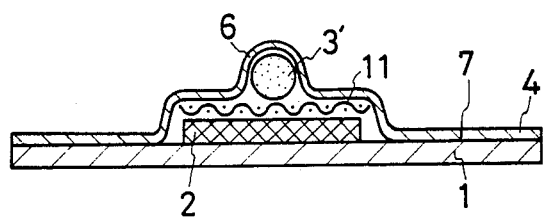

Modified forms of the blister are shown in FIGS. 9 and 10. FIG. 9 shows a blister having the shape of a superior arc, while the blister shown in FIG. 10 has the shape of a modified superior arc. These modified blisters are effective for preventing any capsule material from falling on the pad after rupture of the capsule. The blister shown in FIG. 9 has an opening 10 which is smaller than the diameter of the capsule, but this feature is not equired as for the blister having a modified superior arc profile as shown in FIG. 10. Further, as shown in FIG. 12, a screen 11 or the like may be introduced between the capsule 8 and the pad 2 to facilitate the puncture of the capsule and the removal of the capsule fragments. The screen may be wire mesh, plastic mesh, cloth etc.

Figure 13:
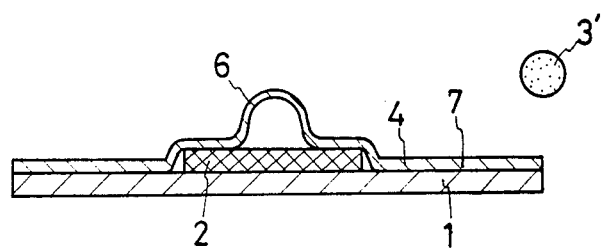

Although the above explanation is made on the embodiments in which the capsule is incorporated into the blister portion in manufacturing the bandage, the invention can be also applied to such an adhesive bandage that an encapsulated medicine is stored in the state that it is disengaged from the blister portion and that is incorporated into the blister portion when use. That is, as shown in FIG. 13, the encapsulated medicine is detached from the blister portion during storage, and when the bandage is applied to a wound, the encapsulated medicine is inserted into the blister portion.

The use of the adhesive bandage of the present invention for applying to the wound was mainly explained here, which, however, does not limit the invention, and the use of the adhesive bandage for a wide purpose is well known by a person skilled in the art.

What is claimed is:

1. An adhesive bandage comprising:
   a. adhesive tape;
   b. an absorbent pad carried by the tape which is smaller in its length and width than the tape; and
   c. a release sheet releasably attached to the tape on the side of the adhesive overlaying the whole pad; said release sheet having:
   d. a blister having an open side facing the pad;
   e. medicine in the blister; and
   f. a medicine covering film for sealing the medicine in the blister responsive to pressure for causing the medicine in the blister to impregnate the pad;
   wherein the medicine is sealingly stored in the blister portion by means of a medicine covering film interposed between the medicine and the adhesive tape;
   wherein the top of the blister is provided with a V-letter shaped or U-letter shaped recessed portion whereby the medicine covering film is ruptured by the bottom of the recessed portion when pressure is applied to the blister.

2. An adhesive bandage claimed in claim 1 wherein a removable ring is interposed between the medicine covering film and the pad to facilitate the rupturing of the film.

3. An adhesive bandage claimed in claim 1, wherein the medicine is held in the blister portion by press through pack.

4. An adhesive bandage claimed in claim 1, wherein the medicine covering film is made from a material selected from the group substantially consisting of aluminum film and glassine paper.

5. An adhesive bandage claimed in claim 1, wherein perforations are provided on the release sheet at both sides of the blister.

6. An adhesive bandage claimed in claim 1, wherein the release sheet is provided with a slit on a place near one end thereof.

7. An adhesive bandage claimed in claim 1, wherein the medicine is selected from the group substantially consisting of sterilizer, disinfectant, wound astringent healing promoter, hemostatic agent, anti-inflammatory agent, antihistamine and local anesthetic.

8. An adhesive bandage claimed in claim 1, wherein the medicine is in a form of solution.

9. An adhesive bandage claimed in claim 1, wherein the medicine is in a form of ointment.

10. An adhesive bandage claimed in claim 1, wherein the medicine is in a form of grease.

11. An adhesive bandage claimed in claim 1, wherein the medicine is in a form of powder.

12. An adhesive bandage claimed in claim 1, wherein the pad is made from a material selected from the group substantially consisting of absorbent cotton, unwoven fabric, paper and sponge.

13. An adhesive bandage claimed in claim 1, wherein the blister portion is designed in a form selected from the group substantially consisting of sphere, ellipse, and rectangle.

14. An adhesive bandage claimed in claim 1 having a plurality of blisters facing a single pad.

15. An adhesive bandage storable with a non-medicated pad which can be simply converted to a medicated pad prior to application of the bandage to a wound; said adhesive bandage comprising:
   a. adhesive tape having an adhesive side and an adhesive-free side; and
   b. an absorbent pad carried by the tape on the adhesive side thereof; and
   c. a release sheet releasably attached to the tape on the adhesive side thereof; said release sheet having:
   d. a blister having an open side facing the pad;
   e. a rupturable film closing the open side of the blister; said rupturable film and said blister together defining a chamber; and
   f. free-flowing medicine in the chamber;
   wherein the blister is more rupture-resistant than is the film such that application of pressure on the outside of the blister causes the film to rupture and further causes the medicine to leave the chamber through the rupture in the film and further causes the medicine to impregnate the pad thereby converting the non-medicated pad to a medicated pad wherein the top of the blister is provided with a V-letter shaped or U-letter shaped recessed portion which serves to engage and rupture the film when pressure is applied to the blister.

16. An adhesive bandage comprising:
   a. adhesive tape having an adhesive side and an adhesive-free side; and
   b. an absorbent pad carried by the tape on the adhesive side thereof, said pad being smaller in length and width than said tape; and
   c. a release sheet releasably attached to the taped on the adhesive side thereof, said release sheet overlaying the whole pad and being releasably attached to said tape around the periphery of said pad; said release sheet having;
   d. a blister having an open side facing the pad;
   e. a rupturable film closing the open side of the blister; said rupturable film and said blister defining a chamber; and
   f. free-flowing medicine in said chamber;
   wherein the blister is more rupture-resistant than is the film such that application of pressure on the outside of the blister causes the film to rupture and further causes the medicine to leave the chamber through the rupture in the film and further causes the medicine to impregnate the pad, and wherein the top of the blister is provided with a V-letter or U-shaped recessed portion which serves to engage and rupture the film when pressure is applied to the blister.

17. An adhesive bandage comprising:
   a. adhesive tape;
   b. an absorbent pad carried by the tape, which is smaller in its length and width than the tape; and
   c. a release sheet releasably attached to the tape on the side of the adhesive overlaying the whole pad; said release sheet having:
   d. a blister having an open side facing the pad and a top opposite the open side, said top of the blister having a V-shaped recess therein;
   e. medicine in the blister; and
   f. a medicine covering film for sealing the medicine in the blister, said medicine covering film being rupturable by the bottom of the V-shaped recess upon the application of pressure to the blister, thereby causing the medicine in the blister to impregnate the pad.

* * * * *